(12) United States Patent
Hartwig et al.

(10) Patent No.: US 8,586,080 B1
(45) Date of Patent: Nov. 19, 2013

(54) INHIBITING CRYSTALLIZATION OF STEROIDAL HORMONES IN TRANSDERMAL DELIVERY SYSTEMS

(75) Inventors: Rod Hartwig, Miami, FL (US); David Kanios, Miami, FL (US)

(73) Assignee: Noven Pharmaceuticals, Inc., Miami, FL (US)

(*) Notice: Subject to any disclaimer, the term of this patent is extended or adjusted under 35 U.S.C. 154(b) by 1802 days.

(21) Appl. No.: 10/975,749

(22) Filed: Oct. 28, 2004

Related U.S. Application Data

(60) Provisional application No. 60/514,960, filed on Oct. 28, 2003.

(51) Int. Cl.
- *A61F 13/00* (2006.01)
- *A61F 13/02* (2006.01)
- *A61K 9/70* (2006.01)
- *A61L 15/16* (2006.01)
- *A61L 15/00* (2006.01)

(52) U.S. Cl.
USPC ........... 424/449; 424/448; 424/445; 424/446; 424/447

(58) Field of Classification Search
USPC .......................... 400/443–449, 78.02–78.07
See application file for complete search history.

(56) References Cited

U.S. PATENT DOCUMENTS

| | | | | |
|---|---|---|---|---|
| 4,737,410 A | * | 4/1988 | Kantner | 428/343 |
| 4,990,339 A | * | 2/1991 | Scholl et al. | 424/443 |
| 5,030,629 A | * | 7/1991 | Rajadhyaksha | 514/211.07 |
| 5,474,783 A | * | 12/1995 | Miranda et al. | 424/448 |

* cited by examiner

*Primary Examiner* — Isis Ghali
(74) *Attorney, Agent, or Firm* — Foley & Lardner LLP

(57) ABSTRACT

Compositions and methods for the continuous and controlled transdermal delivery of an active agent from a pharmaceutically acceptable carrier composition comprising a polyoxazoline polymer, wherein the active drug incorporated in the carrier composition of the transdermal system remains substantially solubilized and stable during storage prior to use.

12 Claims, 1 Drawing Sheet

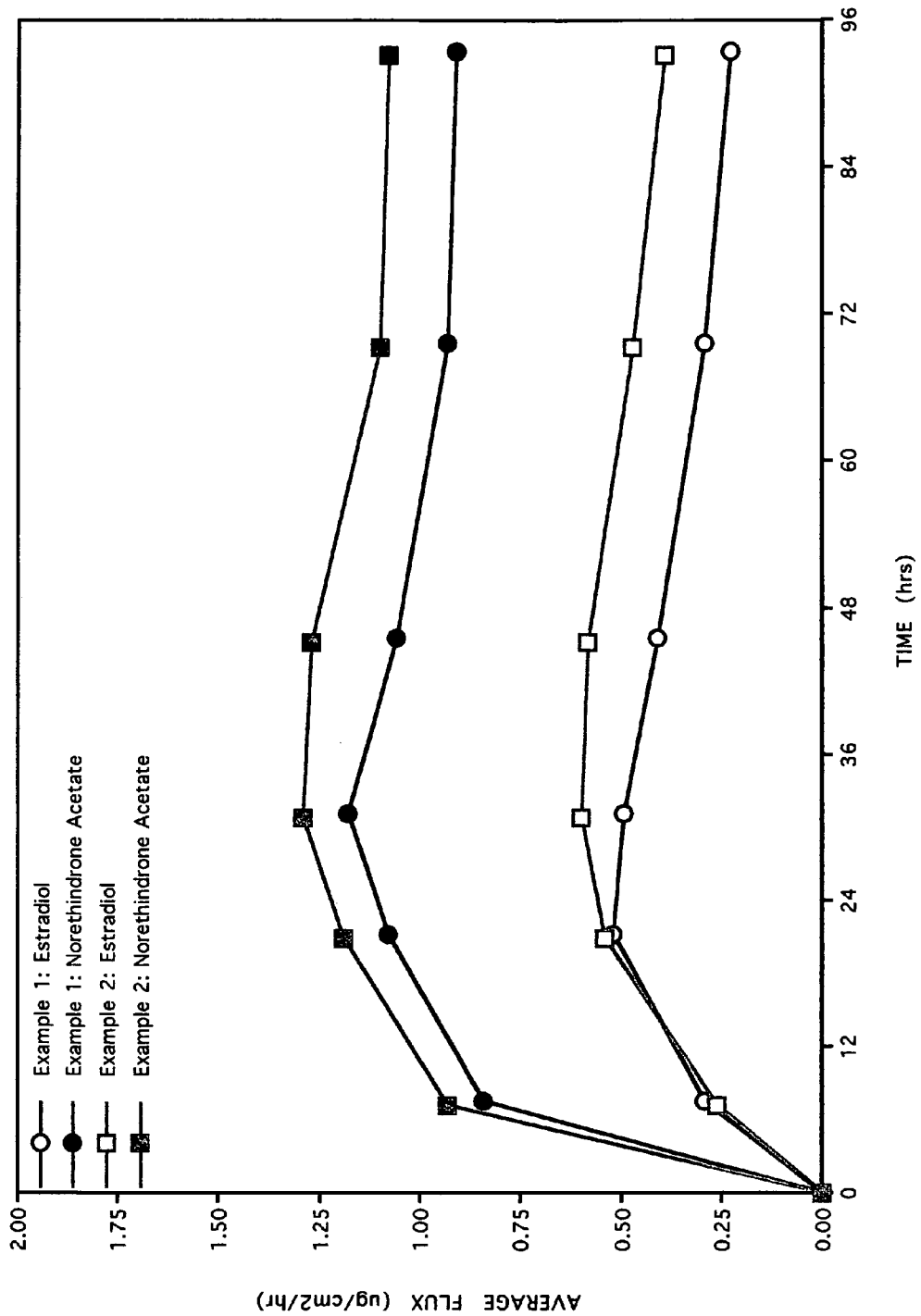

INHIBITING CRYSTALLIZATION OF STEROIDAL HORMONES IN TRANSDERMAL DELIVERY SYSTEMS

CROSS-REFERENCE TO RELATED APPLICATION

This application claims the benefit of U.S. Provisional Application Ser. No. 60/514,960, filed Oct. 28, 2003.

BACKGROUND OF THE INVENTION

This invention relates generally to transdermal drug delivery systems, and more particularly to pressure-sensitive adhesive compositions, that incorporate polyoxaline polymers to inhibit crystal formation and degradation of the active agent in the carrier composition during storage, and improve the delivery rate of the active agent.

The use of transdermal drug delivery systems or "patches" as a means to topically administer a drug is well known. Such systems incorporate the drug into a carrier composition, such as a polymeric and/or pressure-sensitive adhesive composition, from which the drug is delivered at therapeutically effective amounts by absorption through skin or mucosa of the user. Such transdermal systems are described, for example, in U.S. Pat. Nos. 4,814,168; 4,994,267; 5,474,783; and 5,656,286, all of which are expressly incorporated by reference in their entireties.

Transdermal systems that incorporate solid or crystalline forms of drugs require that such drugs be dissolved in the polymeric and/or pressure-sensitive adhesive composition in order to deliver a therapeutically effective amount. The ability of a transdermal system to deliver a therapeutically effective amount for the intended duration of use therefore requires that the active agent remain in non-crystalline or dissolved form in the carrier composition prior to use.

It has been shown that the degree of saturation and solubility of the active agent in the carrier composition are determining factors in controlling delivery of the active agent from the transdermal system. Since only solubilized active agent is available for delivery out of the transdermal system, the carrier composition must not promote drug crystal growth or formation, especially during storage of the system prior to use. It is known that the chemical reactivity between the various components making up the drug carrier composition can significantly affect the drug's solubility in the carrier compositions. For example, many transdermal systems use a pharmaceutically acceptable acrylic polymer as the means to contain the drug. However, it has been found that the functionality and monomeric make-up of such adhesives can significantly affect the drug's solubility in the carrier compositions.

Development of transdermal systems is further frequently hampered by poor solubility of certain active agents in the carrier composition, which in turn also severely limits its therapeutic application. The tendency for crystal formation or growth is known, for example, in the case of high melting point hydrophobic drugs, such as hormones and steroidal active agents, which tend to be poorly soluble or insoluble in polymeric compositions because they form strong crystal bonds.

Failure to control crystal formation and growth can further interfere with the physical properties of the transdermal system. This aspect is particularly important in matrix-type systems because the carrier composition has to be optimized not only to incorporate and administer the desired active agents, but also to obtain sufficient wear properties (means of attachment to the user) for the adhesive carrier. While using low concentrations in order to incorporate the active agent into the carrier may not deleteriously affect the carrier's adhesive properties, low active agent concentration can result in difficulties in achieving an acceptable delivery rate. Poor or inadequate solubility of the active agent can further give rise to crystal formation or growth. Furthermore, surface crystals can come into direct contact with the skin or mucosa and promote irritation.

Generally, concentrations of the active agent substantially at or near the saturation solubility, and even supersaturated (i.e., an amount of active agent at a concentration greater than the solubility of the active agent in the carrier composition at room temperature) are sought in order to increase or maximize delivery rates. Such systems are also desirable because they provide the ability to potentially achieve continuous administration of the active drug in therapeutically effective amounts for prolonged periods of time, such as up to 3 days, and even up to 7 days or more. In these systems, however, the active agent can more easily recrystallize, especially during storage. Crystallization may occur after a few weeks or months of storage.

Active agent that is present in crystalline form cannot be delivered through skin or mucosa, which will accordingly alter drug flux upon application to the user. Inadequate delivery of the active agent in turn leads to blood levels falling below that which are therapeutically effective. The presence of drug crystals is therefore generally undesirable.

The ability of a transdermal system to deliver a therapeutically effective amount for the intended duration of its use further requires that the drug remain stable in its active form (i.e., not substantially decompose, change form or convert into undesirable by-products, metabolites, enantiomers, or substantially inactive or non-therapeutic forms of the drug).

Many transdermal systems rely upon enhancers to improve or increase drug penetration or permeation at the site of topical application of the system. However, certain enhancers may react with drugs to cause their degradation into by-products that can interfere with drug penetration and delivery. See, for example, U.S. Pat. No. 6,024,974.

To prevent drug crystallization and degradation in transdermal systems, compounds which in individual cases have been described in the art as crystallization inhibitors and/or used to improve the storage stability of transdermal systems include PVP, cellulosic polymers, polyethylene oxide, polyvinyl alcohol, polyacrylic acid, gelatins, cyclodextrins, silica, silicon dioxide, starch (derivatives) and dextran. Although the addition of solubilizing agents, such as PVP, help to inhibit crystallization, there are some applications where it is desirable to have greater crystal inhibiting effects or obviate the need for adding a drug degradation inhibitor or stabilizing agent as well.

It has been found that polyoxaline polymers [Poly (2-ethyl-2-oxazoline] are suitable to both suppress or prevent crystal formation and degradation of active agents in transdermal systems, and additionally provide very good in vitro flux rates, particularly with hydrophobic drugs.

SUMMARY OF THE INVENTION

It is therefore an object of this invention to provide a transdermal drug delivery system that can substantially suppress or prevent crystallization of active agents incorporated therein.

It is another object of this invention to provide a transdermal drug delivery system that can substantially suppress or prevent crystallization formation or growth of the active agents incorporated in a pressure-sensitive adhesive carrier composition and delivery a therapeutically effective amount while retaining good physical adhesive properties.

It is also an object of this invention to provide a transdermal drug delivery system that can incorporate active agents that are insoluble or sparingly soluble in pressure-sensitive adhesives in amounts necessary to deliver a therapeutically effective amount without resulting in recrystallization of the active agent after a few weeks or months of storage, and deliver the same at a controlled and predictable release rate.

It is still another object of this invention to provide a method for increasing the solubility and stability of active agents in transdermal delivery systems.

It is additionally an object of this invention to provide a method for making a transdermal drug delivery system that achieves a substantially zero-order kinetic rate of drug delivery for a prolonged period of time without crystallization of the active agent therein.

The foregoing and other objects are achieved by the present invention which provides a transdermal drug delivery system comprising polyoxazoline polymers [poly (2-ethyl-2-oxazoline] in a pharmaceutically acceptable flexible, finite system, wherein the polyoxazoline polymer is present in an amount sufficient to achieve crystallization and degradation inhibition for the active agents incorporated into the carrier composition of the system.

BRIEF DESCRIPTION OF THE DRAWING

FIG. 1 is a graphical representation of the average flux rate of estradiol and norethindrone acetate through cadaver skin from pressure-sensitive adhesive carrier compositions of the present invention comprising a polyoxazoline polymer as compared to a pressure-sensitive adhesive carrier composition comprising PVP. The graph illustrates the type of delivery kinetics which can be achieved from an adhesive carrier composition of the present invention comprising polyoxazoline and demonstrates increased drug delivery for an extended duration at a substantially zero-order rate from a transdermal system of the present invention.

DETAILED DESCRIPTION OF THE INVENTION

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage of an active agent into and/or through skin or mucosa for localized or systemic delivery.

The term "solubilized" is intended to mean that in the carrier composition there is an intimate dispersion or dissolution of the active agent at the crystalline, molecular or ionic level, such that crystals of the active agent cannot be detected using a microscope having a magnification of 25×. As such, the active agent is considered herein to be in "non-crystallized" form when in the compositions of the present invention.

The term "flux" is defined as the absorption of the drug through the skin or mucosa, and is described by Fick's first law of diffusion:

$$J = -D(dCm/dx),$$

Where J is the flux in $g/cm^2/sec$, D is the diffusion coefficient of the drug through the skin or mucosa in $cm^2/sec$ and Dcm/dx is the concentration gradient of the drug across the skin or mucosa.

The term "degrade" or "degradation" as used herein refers to any change in the active form of the drug within the transdermal device during storage, for example by hydrolysis and/or oxidation of the drug or interaction with permeation enhancers, matrix materials, and any other excipients contained within the transdermal system and environmental factors such as air, light, moisture vapor, water (in liquid or vapor form), oxygen, and the like which cause an undesirable by-product, metabolite, enantiomer, or substantially inactive or non-therapeutic form of the drug.

The phrase "pharmaceutically acceptable flexible, finite" as used herein is intended to mean a solid form capable of conforming to a surface to which it is applied, and which is capable of maintaining the contact in such solid form so as to facilitate topical application without adverse physiological response, and without being appreciably decomposed by aqueous contact during use by a subject.

The term "user" or "subject" as used herein is intended to include all warm-blooded mammals, preferably humans.

The phrase "substantially zero-order" as used herein means transdermal delivery of an active agent at a release rate which is approximately constant once steady state is attained, typically within 12 to 24 hours after topical application. While variability in blood levels of active agent are contemplated within the scope of this meaning once steady state release is attained, the depletion rate of active agent over the duration of use should typically not exceed about 20% to about 30%.

The term "drug" (and its equivalents "active agent," "bioactive agent," "medicament" and "pharmaceutical") as used herein is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. Also within the invention are such bioactive agents as pesticides, insect repellents, sun screens, cosmetic agents, etc. It should be noted that the drugs and/or bioactive agents may be used singularly or as a mixture of two or more such agents, and in amounts sufficient to prevent, cure, diagnose or treat a disease or other condition, as the case may be.

The drugs and mixtures thereof are used in a "therapeutically effective amount." This term means that the concentration of the drug is such that in the composition it results in a therapeutic level of drug delivered over the term that the transdermal dosage form is to be used, preferably with zero-order kinetics.

The drugs and mixtures thereof contained in the carrier composition can be in different forms depending on the solubility and release characteristics desired, for example as neutral molecules, components of molecular complexes, and pharmaceutically acceptable salts, free acids or bases, or quaternary salts of the same. Simple derivatives of the drugs such as pharmaceutically acceptable ethers, esters, amides and the like which have desirable retention and release characteristics but which are easily metabolized at body pH, and enzymes, pro-active forms, pro-drugs and the like, can also be employed.

There is no limitation on the type of drugs that can be used in this invention. These drugs include but are not limited to those categories and species of drugs set forth on page ther-1 to ther-28 of the Merck Index, 12th Edition Merck and Co. Rahway, N.J. (1999). This reference is incorporated by reference in its entirety. However, drugs that are solid at room temperature are preferred.

Steroidal hormones and active agents that generally tend to be poorly soluble or insoluble in pressure-sensitive adhesive carrier compositions are preferred and include, for example, Estrogenically effective steroid hormones such as Colpormon, Conjugated Estrogens, Estradiol (17β- and α-) and its Esters (e.g., Acetate, Benzoate, Cypionate, Dipropionate Diacetate, Enanthate, Undecylate and Valerate), Estriol, Estrone, Ethinyl Estradiol, Equilenin, Equilin, Mestranol, Moxestrol, Mytatrienediol, Quinestradiol and Quinestrol; Progestagenically effective steroid hormones such as Allylestrenol, Anagestone, Chlormadinone Acetate, Delmadinone Acetate, Demegestone, Desogestrel, 3-Keto Desogestrel, Dimethisterone, Dydrogesterone, Ethinylestrenol, Ethisterone, Ethynodiol (and Diacetate), Fluorogestone Acetate, Gestodene, Gestonorone Caproate, Haloprogesterone, (17-Hydroxy- and 17-Acetate-) 16-Methylene-Progesterone, 17α-Hydroxyprogesterone (Acetate and Caproate), Levonorgestrel, Lynestrenol, Medrogestone, Medroxyprogesterone (and Acetate), Megestrol Acetate, Melengestrol, Norethindrone (Acetate and Enanthate), Norethisterone, Norethynodrel, Norgesterone, Norgestimate, Norgestrel, Norgestrienone, 19-Norprogesterone, Norvinisterone, Pentagestrone, Progesterone, Promegestone, Quingestrone and Trengestone; Androgenically effective steroid hormones such as Aldosterone, Androsterone, Boldenone, Cloxotestosterone, Dehydroepiandrosterone, Fluoxymesterone, Mestanolone, Mesterolone, Methandrostenolone, Methyltestosterone, 17α-Methyltestosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone (Acetate, Enanthate, Isobutyrate, Propionate and Undecanoate), Testosterone 17-Chloral Hemiacetal, Testosterone 17β-Cypionate and Tiomesterone.

Particularly preferred drugs include estrogens and progestins such as estradiol, norethindrone and norethindrone acetate, alone or in combination.

The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically selected so as to provide transdermal delivery characterized by a zero order time dependency for a prolonged period of time. The minimum amount of drug in the system is selected based on the amount of drug which passes through the skin in the time span for which the device is to provide therapy. Normally, the amount of drug in the system can vary from about 0.01% to about 50%, or more preferably from about 0.1% to 30% by weight based on the dry weight of total carrier composition. However, the composition of this invention is particularly useful for drugs which are used in relatively low concentrations, especially from about 0.5% to about 20% by weight based on the dry weight of total carrier composition.

The term "carrier" as used herein refers to any non-aqueous, pharmaceutically acceptable material known in the art as suitable for transdermal drug delivery administration, and includes any polymeric material into which an active agent may be solubilized in combination or admixture with the other ingredients of the composition.

The carrier material is typically used in an amount of about 20% to about 98%, and preferably from about 30% to about 95%, and most preferably about 40% to about 95% by weight based on the dry weight of the total carrier composition. The term "carrier composition" may also refer to enhancers, solvents, co-solvents and other types of addictives useful for facilitating transdermal drug delivery.

Suitable carrier materials include all of the non-toxic natural and synthetic polymers known for or suitable for use in transdermal systems, such as solvent-based, hot melt and grafted, and may be used alone or in combinations, mixtures or blends. Examples include acrylic polymers, gums, silicone-based polymers (broadly referred to as "polysiloxanes" and including silicone fluids) and rubber-based adhesives that include hydrocarbon polymers such as natural and synthetic polyisoprene; polybutylene; polyisobutylene; styrene based polymers; styrene block copolymers; butadiene based polymers; styrene/butadiene polymers; styrene-isoprene-styrene block copolymers; hydrocarbon polymers such as, for example, butyl rubber; halogen-containing polymers such as, for example, polyacrylonitrile, polytetrafluoroethylene, polyvinylchloride, polyvinylether, polyvinylidene chloride, and polychlorodieneas polyisobutylenes, polybutylenes, ethylene/vinyl acetate and vinyl acetate based copolymers, styrene/butadiene copolymers, polyisoprenes, styrenes and styrene block copolymers and block amide copolymers, and bioadhesives set forth in U.S. Pat. No. 6,562,363 which is expressly incorporated by reference in its entirety.

The polymeric materials preferably comprise adhesives and, in the most preferred embodiment, the carrier composition is a pressure-sensitive adhesive. An "adhesive" as used herein means any natural or synthetic substance that is capable of sticking to the site of topical application. The term "pressure-sensitive adhesive" as used herein refers to an adhesive which adheres instantaneously to most surfaces with the application of very slight pressure and remains permanently tacky. An adhesive is a pressure-sensitive adhesive within the meaning of that term as used herein if it has the properties of an adhesive pressure-sensitive adhesive per se or functions as the same by admixture with tackifiers, plasticizers, cross-linking agents or other additives. The term pressure-sensitive adhesive also includes mixtures of different polymers and mixtures of polymers, such as polyisobutylenes of different molecular weights, the resultant mixtures being a pressure-sensitive adhesive. In the last case, the polymers of lower molecular weight in the mixture are not considered to be "tackifiers," said term being reserved for additives which differ other than in molecular weight from the polymers to which they are added.

Suitable polysiloxanes include silicone pressure-sensitive adhesives which are based on two major components: a polymer, or gum, and a tackifying resin. The polysiloxane adhesive is usually prepared by cross-linking the gum, typically a high molecular weight polydiorganosiloxane, with the resin, to produce a three-dimensional silicate structure, via a condensation reaction in an appropriate organic solvent. The ratio of resin to polymer is the most important factor which can be adjusted in order to modify the physical properties of polysiloxane adhesives. Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, N.Y. (1989).

Further details and examples of silicone pressure-sensitive adhesives which are useful in the practice of this invention are described in the following U.S. Pat. Nos. 4,591,622; 4,584,355; 4,585,836; 4,655,767 and 6,337,086. Suitable silicone pressure-sensitive adhesives are commercially available and include the silicone adhesives sold under the trademarks BIO-PSA® by Dow Corning Corporation, Medical Products, Midland, Mich.

In particularly preferred embodiments of the invention, the carrier matrix composition comprises a blend of one or more acrylic, polysiloxane and/or rubber-based polymers, particularly an acrylic and polysiloxane polymer.

The term "acrylic" is intended to be used interchangeably with the terms acrylate, polyacrylate and polyacrylic as used herein and as known in the art.

The acrylic polymers useful in practicing the invention are polymers of one or more monomers of acrylic acids and other copolymerizable monomers. The acrylic polymers also include copolymers of alkyl acrylates and/or methacrylates and/or copolymerizable secondary monomers or monomers with functional groups. By varying the amount of each type of monomer added, the cohesive properties of the resulting acrylic polymer can be changed as is known in the art. In general, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylamino ethyl acrylate, tert-butylaminoethyl methacrylate, methoxyethyl acrylate and methoxyethyl methacrylate and other monomers having at least one unsaturated double bond which participates in copolymerization reaction in one molecule and a functional group on its side chain such as a carboxyl group, a hydroxyl group, a sulfoxyl group, an amino group, an amino group and an alkoxyl, as well as a variety of other monmeric units including alkylene, hydroxy-substituted alkylene, carboxylic acid-substituted alkylene, vynylalkanoate, vinylpyrrolidone, vinylpyridine, vinylpirazine, vinylpyrrole, vinylimidazole, vinyl caprolactam, vinyl oxazole, vyinlacate, vinylpropionate and vinylmorpholine.

Further details and examples of acrylic polymers which are suitable in the practice of the invention are described in Satas, "Acrylic Adhesives," Handbook of Pressure-Sensitive Adhesive Technology, 2.sup.nd ed., pp. 396-456 (D. Satas, ed.), Van Nostrand Reinhold, N.Y. (1989).

Suitable acrylic polymers and adhesives are commercially available and include those sold under the trademarks DURO-TAK® by National Starch Company, Bridgewater, N.J.; GELVA® by Surface Specialties, Springfield, Mass.; and EUDRAGIT® by Roehm Pharma GmbH, Darmstadt, Federal Republic of Germany.

In the practice of preferred embodiments of the invention, the silicone-based polymer constitutes from about 9% to about 97% of the total weight of the pressure-sensitive adhesive composition, preferably about 12% to about 97%, and more preferably from about 14% to about 94%, and most preferably from about 18 to 90% of the total weight of the carrier material.

The polymeric materials preferably comprise adhesives and, in particular, pressure-sensitive adhesives. The carrier material is typically used in an amount of about 10% to about 90%, and preferably from about 10% to about 75%, by weight based on the dry weight of the total carrier composition.

The term "carrier composition" may also refer to enhancers, solvents, co-solvents and other types of additives useful for facilitating transdermal drug delivery.

For drug molecules which are not readily soluble in the polymer system of the present invention containing polyoxazoline polymers, another solvent or "co-solvent" for the drug and polymer can be added. Such solvents and/or co-solvents are those known in the art, and are non-toxic, pharmaceutically acceptable substances, preferably liquids, which do not substantially negatively affect the adhesive properties or the solubility of the active agents at the concentrations used. The solvent and/or co-solvent can be for the active agent or for the carrier materials, or both.

Suitable solvents include volatile liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate isobutyl isobutyrate, hexyl acetate, 2-ethylhexyl acetate or butyl acetate); and combinations and mixtures thereof.

Suitable co-solvents include polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, and the like.

Further suitable co-solvents include glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids.

Although the exact amount of co-solvents that may be used in the carrier composition depends on the nature and amount of the other ingredients, such amount typically ranges from about 0.1% to about 40%, and preferably from about 0.1% to about 30% by weight, and more preferably from about 1% to about 20%, by weight based on the dry weight of the total carrier composition.

In certain embodiments of the invention, an enhancer is incorporated into the carrier composition. The term "enhancers" as used herein refers to substances used to increase permeability and/or accelerate the delivery of an active agent through the skin or mucosa, and include monhydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene (4) lauryl ether, polyoxyethylene (2) oleyl ether and polyoxyethylene (10) oleyl ether commercially available under the trademark BRIJ®. 30, 93 and 97 from ICI Americas, Inc., and BRIJ® 35, 52, 56, 58, 72, 76, 78, 92, 96, 700 and 721; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85. Other suitable enhancers include oleic and linoleic acids, triacetin, ascorbic acid, panthenol, butylated hydroxytoluene, tocopherol, tocopherol acetate, tocopheryl linoleate. If enhancers are incorporated into the carrier composition, the amount typically ranges up to about 30%, and more preferably from about 0.1% to about 15% by weight based on the dry weight of the total carrier composition.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. Additional additives include binders such as lecithin which "bind" the other ingredients, or rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the final composition. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the carrier composition. Such additives or excipients are typically used in amounts up to 25%, and more preferably from about 0.1% to about 10% by weight based on the dry weight of the total carrier composition.

For both crystal inhibition and degradation inhibition as well as improved permeation of active agents in transdermal drug delivery systems, particularly those containing hormonal or steroidal active agents in pressure-sensitive adhesive carrier compositions, polyoxazoline was added to transdermal drug delivery systems according to the invention. By their addition to such carrier compositions, the active agent is able to remain solubilized and stable during storage while demonstrating very good in vitro flux rates.

Polyoxazoline is a polymer with similar chemical moieties to PVP. Both PVP and Polyoxazoline contain repeating tertiary amines and carbonyl groups. Both polymers are available in similar molecular weight ranges and offer similar solubility in polar, organic solvents. Poly (2-ethyl-2-oxazoline) is offered as a substitute in industrial adhesive applications for polyvinyl alcohol and PVP.

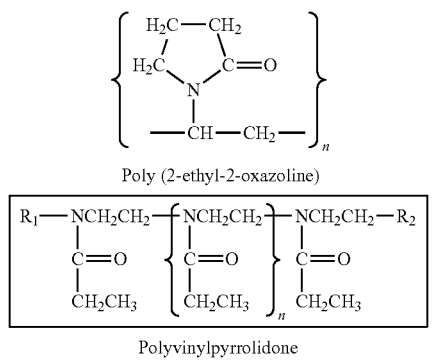

Poly (2-ethyl-2-oxazoline)

Polyvinylpyrrolidone

Polyoxazoline polymers are commercially available in varying molecular weights, and include those sold under the trademarks Aquazol® by Polymer Chemistry Innovations, Inc., Tucson, Ariz. Polyoxazoline polymers having a molecular weight of about 200,000 or less are preferred in order maintain their polarity. The polyoxazoline polymer is preferably present in the carrier composition in an amount ranging from about 1% to about 25% by weight of the total carrier composition, more preferably from about 5%-20%, and most preferably from about 5%-15%. In a carrier composition embodiment of the invention, a multiple polymer adhesive system comprises a blend of 14-94% by weight of a polysiloxane or rubber-based polymer, 5-85% of a polyacrylate polymer, 1-15% of a polyoxazoline polymer, 0.1-30 drugs, 0-20% enhancer, and 0-30% co-solvents for the drugs, wherein the multiple polymer adhesive system comprises about 40-95% by weight of the total carrier composition.

In the preferred embodiment of the present invention, wherein the carrier is a pressure-sensitive adhesive comprising a blend of polymers, an exemplary general method of preparation is as follows:

1. Appropriate amounts of polyoxazoline, volatile polar and/or non-polar organic liquid(s) such as those previously described as suitable solvent(s) or co-solvent(s) (for example toluene), with or without enhancer(s), are combined and thoroughly mixed together in a vessel.

2. The drug is then added to the mixture and agitation is carried out until the drug is uniformly mixed in.

3. Appropriate amounts of polysiloxane and polyacrylate are then added to the drug mixture, and thoroughly mixed.

4. The mixture of the carrier composition is then transferred to a coating operation where it is formed into a layer, preferably by coating or casting at a controlled specified thickness at ambient temperature, onto a flexible sheet material, such as a release liner, followed by evaporation of the volatile processing solvents at elevated temperatures (e.g., by passing through an oven). The non-volatile or higher boiling point solvents and/or co-solvents used in the carrier composition remain therein. The formulation where it is coated onto a protective release liner at a controlled specified thickness. The coated product is then passed through an oven in order to drive off all volatile processing solvents.

5. The dried carrier composition that has been coated or cast on the flexible sheet material is then laminated or joined to another flexible sheet material, preferably a backing layer, and wound into rolls for further processing.

6. Appropriate size and shape individual transdermal drug delivery systems are cut from the roll material and then packaged (e.g., pouched).

The order of steps, the amount of the ingredients, and the amount and time of mixing may be important process variables which will depend on the specific polymers, active agents, solvents and/or co-solvents, enhancers and additives and excipients used in the composition. These factors can be adjusted by those skilled in the art, while keeping in mind the objects of achieving a solubilized active agent and providing a uniform product that will also give desirable results. It is believed that a number of other methods, including changing some of the order of steps, can be carried out and will give desirable results. In addition to having various shapes, the dosage units produced may come in various sizes. Illustratively, a single dosage unit may have a surface area in the range of 1 to 200 $cm^2$. Preferred sizes are from 5 to 60 $cm^2$.

Further details and examples of pressure-sensitive adhesives, enhancers, solvents, co-solvents, and other additives, as well as transdermal systems generally, suitable in practicing the invention are described in U.S. Pat. Nos. 5,474,787 and 5,656,286 which are assigned to Noven Pharmaceuticals, Inc. and incorporated herein by reference.

The device, or individual dosage unit, of the present invention can be produced in any manner known to those of skill in the art. After the carrier composition is formed, it may be brought into contact with the backing layer in any manner known to those of skill in the art. Such techniques include calendar coating, hot melt coating, solution coating, etc. Of course, backing materials are well known in the art and can comprise plastic films of polyethylene, vinyl acetate resins, polyester, polypropylene, BAREX®, ethylene/vinyl acetate copolymers, polyvinyl chloride, polyurethane, and the like, metal foils, non-woven fabric, cloth, in coextrusions or laminations of the above and commercially available laminates. The backing material generally has a thickness in the range of 2 to 1000 micrometers.

Suitable materials that can be used, singularly, in combination, as laminates or as coextrusions, to form the release liner are well known in the art. When the release liner is composed of a material which typically does not readily release (i.e., is not easily removed or separated from the carrier composition), for example paper, a coating material such as a silicone may be applied to the release liner by any conventional means. Preferred release liners are films commercially available from DuPont, Wilmington, Del., under the trademark Mylar®, from Rexam Release, Oak Brook, Ill. under the trademark FL2000® and MRL2000®, and from 3M Corporation, St. Paul, Minn. under the trademark Scotch-Pak®.

It is understood that a reservoir-type transdermal system, provided with a separate pressure-sensitive adhesive layer or adhesive means of attachment, is contemplated in practicing the invention and may well be of advantage in certain cases. The reservoir-type system may further consist of one or more layers or membranes. Regardless of the type of transdermal system used to practice the invention, the carrier composition is preferably non-aqueous (i.e., substantially free of water).

EXAMPLES

The above description and following specific examples are hereby illustrative of pharmaceutically acceptable active agent carrier compositions and transdermal drug delivery systems, and methods of making same, within the contemplation of the invention. The description and examples are in no way intended to be, or should be considered, limiting of the scope of the invention. And while efforts have been made to ensure accuracy with respect to numbers used (such as amounts and temperatures), some experimental error and deviation should be accounted for and/or allowed.

Evaluation of Poly (2-ethyl-2-oxazoline) on drug crystallization, degradation, permeation and delivery was performed in combination hormone transdermal drug delivery systems containing estradiol and norethindrone acetate.

Example 1

An estradiol/norethindrone acetate pressure-sensitive adhesive mixture was prepared by combining 5.68 grams of a polyoxazoline polymer [Aquazol® 50] with 5.68 grams of isopropyl alcohol and 5.71 grams of toluene. Then 66.41 grams of a polysiloxane adhesive (BIO-PSA®-4603, trimethylated silica treatment with dimethyl siloxane in toluene; Dow Corning Corporation, Medical Products, Midland, Mich.), 8.74 grams of a polyacrylate adhesive (Gelva® 737, an acrylic resin in ethyl acetate, ethanol and toluene; Surface Specialties, Springfield, Mass.), 2.27 grams of dipropylene glycol and 3.41 grams of oleic acid were added as co-solvents and enhancers, and thoroughly mixed in an appropriate container until the mixture was completely homogeneous. The resulting composition had the ingredient concentrations on a dry weight percent basis (i.e., after evaporation of the volatile solvents) as shown below.

TABLE 1

| INGREDIENT | WEIGHT % |
| --- | --- |
| Polysiloxane Adhesive | 71.3 |
| Polyacrylate Adhesive | 5.0 |
| Polyoxazoline | 10.0 |
| Dipropylene Glycol | 4.0 |
| Oleic Acid | 6.0 |
| Estradiol | 0.7 |
| Norethindrone Acetate | 3.0 |
|  | 100.0 |

The method of Example 1 was used with appropriate amounts of the same starting materials, except that PVP [Kollidon® 30, soluble polyvinylpyrrolidone polymer made by BASF AG, Ludwigshafen, Germany] was used in place of polyoxazoline, to yield the same ingredient concentrations by dry weight for Example 2. Example 2 is presented as a control formulation to demonstrate the effect of polyoxazoline polymers.

The blends of Example 1 and 2 were each cast with a wet gap applicator bar onto a fluoropolymer coated polyester release liner (ScotchPak® 1022). The castings were dried for 5 minutes at ambient room temperature (RT) and relative humidity (RH) and then for 5 minutes at 92° C. in a convection air oven. Upon completion of drying, the dry castings were pressure laminated to the ethylene/vinyl acetate side of a polyester/ethylene vinyl acetate backing film (ScotchPak® 9732). The dried carrier composition had a coat weight of approximately 10 mg/$cm^2$.

Degradation Study

The resulting laminates for Examples 1 and 2 were die cut into 10 $cm^2$ samples and three samples each were packaged into a paper/foil/polyethylene pouchstock to evaluate degradation. The pouched samples were maintained at ambient RT and RH and at 80° C. for 4 days. The 4-day 80° C. accelerated aging study has been proven through repeated experimentation to produce a related substance formation indicative of long term room temperature storage conditions for transdermal systems as experienced during storage prior to use. The samples were subjected to analysis by high pressure liquid chromatography (HPLC) to determine formation of any degradents (drug related substances).

TABLE 2

|  | Example 2 | Example 1 |
|---|---|---|
| Estradiol Related Substances (4-day RT/RH) | 0.67% | 0.41% |
| Estradiol Related Substances (4-day 80° C.) | 12.78% | 8.41% |
| Norethindrone Acetate Related Substances (4-day RT/RH) | 0.63% | 0.51% |
| Norethindrone Acetate Related Substances (4-day 80° C.) | 10.87% | 6.72% |

Table 2 presents the average total related substance formation (i.e., drug degradants) for estradiol and norethindrone acetate at ambient RT/RH and 4-day 80° C. As can be seen in Table 2, the RT/RH storage condition exhibits a slight decrease in total related substances for the example containing polyoxazoline versus the PVP containing example. At 80° C., there is a dramatic decrease in related substance formation, a 36% reduction for estradiol and a 38% reduction for norethindrone acetate, in Example 1.

Flux Study

Human cadaver skin permeation studies were performed to determine drug permeation through the stratum corneum barrier layer. The stratum corneum was obtained from split thickness, cryo-preserved cadaver skin by the heat separation technique. Three samples each of 5/16" diameter were cut from the resulting laminates of Examples 1 and 2 and mounted onto Y2" diameter pieces of the stratum corneum, then placed on modified Franz diffusion cells. The receptor area of the cell was filled in 7.5 mL of 0.9% NaCl and 0.01% $NaN_3$ in deionized water. The cells were maintained at a constant 32° C. and the receptor solution was magnetically stirred at approximately 300 rpm. At specified time points, samples of the receptor phase were taken with complete replacement of the receptor phase. The samples were tested by HPLC for drug content. The cumulative permeation rate over an 84 hour time period for each of the two drugs was compared and the results set forth in Table 3.

TABLE 3

|  | Cumulative Estradiol Permeation ($\mu g/cm^2/84$ hrs) | Cumulative Norethindrone Acetate Permeation ($\mu g/cm^2/84$ hrs) |
|---|---|---|
| Example 2 | 31.49 | 84.59 |
| Example 1 | 42.08 | 97.98 |

Results from the composition containing polyoxazoline indicate the permeability of both drugs has been increased by the addition of that polymer. Estradiol permeation increased by approximately 34% and norethindrone acetate permeation increased by approximately 16%.

Crystal Growth Study

The resulting laminates of Examples 1 and 2 were cut into approximately 1"×4" strips and maintained at ambient RT/RH (20-22° C. and a relative humidity of 60-70%). The rate of crystal formation was compared over varying time periods and the incidence of crystal formation is set forth in Table 4. Crystal growth is defined as the number of crystals visible by the naked eye with confirmation by a low power microscope (25× magnification).

TABLE 4

| | # of Visible Crystals | | | | |
|---|---|---|---|---|---|
| | 1 day | 7 days | 30 days | 60 days | 90 days |
| Example 2 | None | 50 | 55 | 62 | 100 |
| Example 1 | None | None | None | None | 12 |

Example 2 grows a significant amount of visible crystals within one weeks' time. Example 1 continues to be crystal free through approximately 3 months' time, with minimal crystal formation thereafter.

The incorporation of Poly (2-ethyl-2-oxazoline) into transdermal carrier compositions demonstrates significant decreases in both crystal growth and related substance formation. More surprisingly, the polyoxazoline containing carrier demonstrates a significant increase in skin permeation and a more sustained delivery profile over the 3.5 day delivery period.

TABLE 5

| Results of Comparative Studies | | |
|---|---|---|
| Study | Example 2 | Example 1 |
| Crystal Growth (# of visible crystals) | >100 | 20 |
| Estradiol Related Substances (%) | 12.78% | 8.14% |
| Norethindrone Acetate Related Substances (%) | 10.87% | 6.72% |
| Estradiol Skin Permeation Rate | 0.36 $\mu g/cm^2/hr$ | 0.49 $\mu g/cm^2/hr$ |
| Norethindrone Acetate Skin Permeation Rate | 1.00 $\mu g/cm^2/hr$ | 1.16 $\mu g/cm^2/hr$ |

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A transdermal drug delivery system comprising
    a pharmaceutically acceptable carrier composition comprising a blend of:
    (i) one or more polymers selected from the group consisting of polyacrylates, polysiloxanes, silicone fluids, rubbers, gums, polyisobutylenes, polyvinylethers, polyurethanes, styrene block copolymers, styrene/butadiene polymers, polyether block amide copolymers, ethylene/vinyl acetate copolymers, and vinyl acetate based polymers;
    (ii) a crystallization inhibiting effective amount of a polyoxazoline polymer in an amount from about 1% to about 25% by weight, based on the dry weight of the total carrier composition; and
    (iii) a therapeutically effective amount of one or more active agents, wherein said one or more active agents comprises a steroidal hormone and wherein said amount comprises from about 0.01% to about 50% by weight, based on the dry weight of the total carrier composition.

2. The transdermal drug delivery system of claim 1, wherein said steroidal hormone comprises an estrogen or progestin.

3. The transdermal drug delivery system of claim 1, comprising a polyacrylate polymer and a polysiloxane polymer.

4. The transdermal drug delivery system of claim 1, comprising a polyacrylate polymer and a rubber-based polymer.

5. The transdermal drug delivery system of claim 1, wherein said polyoxazoline is present in an amount of from about 5% to 20% by weight, based on the dry weight of the total carrier composition.

6. The transdermal drug delivery system of claim 1, wherein said polyoxazoline is present in an amount of from about 5% to 15% by weight, based on the dry weight of the total carrier composition.

7. The transdermal drug delivery system of claim 1, further comprising a cosolvent for one or more of said one or more active agents.

8. The transdermal drug delivery system of claim 7, wherein said cosolvent comprises dipropylene glycol.

9. The transdermal drug delivery system of claim 1, further comprising an enhancer.

10. The transdermal drug delivery system of claim 9, wherein said enhancer comprises oleic acid.

11. The transdermal drug delivery system of claim 1, comprising:
  14-94% by weight of a polysiloxane or rubber-based polymer;
  5-85% by weight of a polyacrylate polymer;
  1-15% by weight of a polyoxazoline polymer;
  0.1-30% by weight of one or more active agents;
  0-20% by weight of an enhancer, and
  0-30% by weight of a cosolvent for one or more of said one or more active agents,
  all based on the dry weight of the total carrier composition.

12. A method of inhibiting crystal formation of an active agent in a transdermal drug delivery system according to claim 1, comprising forming a blend comprising components (i), (ii), and (iii).

* * * * *